(12) United States Patent
Kringle et al.

(10) Patent No.: US 11,241,245 B2
(45) Date of Patent: Feb. 8, 2022

(54) TISSUE DEFLECTING DEVICES AND RELATED METHODS OF USE

(71) Applicants: Boston Scientific Scimed, Inc., Maple Grove, MN (US); University of Massachusetts, Boston, MA (US)

(72) Inventors: Mark Kringle, Minneapolis, MN (US); Devon N. Arnholt, Shoreview, MN (US); Mark W. Boden, Harrisville, RI (US); David Shreeve, Northborough, MA (US); Joel T. Eggert, Plymouth, MN (US); Christopher Macomber, Wayzata, MN (US); Danilo Decio, Worcester, MA (US)

(73) Assignees: BOSTON SCIENTIFIC SCIMED, INC., Maple Grove, MN (US); UNIVERSITY OF MASSACHUSETTS, Boston, MA (US)

( * ) Notice: Subject to any disclaimer, the term of this patent is extended or adjusted under 35 U.S.C. 154(b) by 431 days.

(21) Appl. No.: 15/978,229

(22) Filed: May 14, 2018

(65) Prior Publication Data
US 2018/0325540 A1    Nov. 15, 2018

Related U.S. Application Data

(60) Provisional application No. 62/506,289, filed on May 15, 2017.

(51) Int. Cl.
*A61B 17/29* (2006.01)
*A61B 17/32* (2006.01)
(Continued)

(52) U.S. Cl.
CPC .......... *A61B 17/29* (2013.01); *A61B 17/0218* (2013.01); *A61B 17/320016* (2013.01);
(Continued)

(58) Field of Classification Search
CPC .. A61B 2017/00314; A61B 2017/2939; A61B 2017/3443; A61B 2017/2908;
(Continued)

(56) References Cited

U.S. PATENT DOCUMENTS 5,916,147 A    6/1999 Boury
6,190,399 B1   2/2001 Palmer et al.
(Continued)

FOREIGN PATENT DOCUMENTS

WO    2013/039999 A2    3/2013

*Primary Examiner* — Anh T Dang
(74) *Attorney, Agent, or Firm* — Bookoff McAndrews, PLLC

(57) ABSTRACT

A medical device may include a plurality of links reciprocally movable between a loose configuration having a first rigidity and a compact configuration having a second rigidity greater than the first rigidity, wherein application of a force to a distalmost link of the plurality of links when the plurality of links are in the loose configuration causes the plurality of links to change orientation relative to one another, and application of the force to the distalmost link when the plurality of links are in the compact configuration does not cause the plurality of links to change orientation relative to one another.

19 Claims, 9 Drawing Sheets

(51) Int. Cl.
*A61B 17/34* (2006.01)
*A61B 17/02* (2006.01)
*A61B 17/30* (2006.01)
*A61B 17/00* (2006.01)
*A61B 17/3205* (2006.01)
*A61B 18/14* (2006.01)
*A61B 90/50* (2016.01)
*A61B 90/30* (2016.01)
*A61B 90/00* (2016.01)
*A61B 34/30* (2016.01)

(52) U.S. Cl.
CPC ...... *A61B 17/3415* (2013.01); *A61B 17/3478* (2013.01); *A61B 17/30* (2013.01); *A61B 17/32056* (2013.01); *A61B 18/1492* (2013.01); *A61B 90/30* (2016.02); *A61B 90/361* (2016.02); *A61B 2017/00314* (2013.01); *A61B 2017/00367* (2013.01); *A61B 2017/00477* (2013.01); *A61B 2017/00849* (2013.01); *A61B 2017/2908* (2013.01); *A61B 2017/2937* (2013.01); *A61B 2017/2939* (2013.01); *A61B 2017/320032* (2013.01); *A61B 2017/345* (2013.01); *A61B 2017/3443* (2013.01); *A61B 2017/3445* (2013.01); *A61B 2017/3452* (2013.01); *A61B 2034/306* (2016.02); *A61B 2090/3937* (2016.02); *A61B 2090/508* (2016.02)

(58) Field of Classification Search
CPC .. A61B 2017/2937; A61B 2017/00367; A61B 17/29; A61B 17/3478; A61B 17/0218; A61B 17/3415; A61B 17/320016; A61B 18/1492
See application file for complete search history.

(56) References Cited

U.S. PATENT DOCUMENTS

| | | | |
|---|---|---|---|
| 8,153,181 | B2 | 4/2012 | Holman et al. |
| 8,382,770 | B2 | 2/2013 | DeLegge et al. |
| 2005/0090711 | A1 | 4/2005 | Fuchs et al. |
| 2006/0058582 | A1 | 3/2006 | Maahs et al. |
| 2006/0293612 | A1 | 12/2006 | Jenson et al. |
| 2007/0135803 | A1 | 6/2007 | Belson |
| 2009/0234280 | A1 | 9/2009 | Tah et al. |
| 2012/0071720 | A1* | 3/2012 | Banik ............... A61B 1/00045 600/118 |
| 2014/0012287 | A1 | 1/2014 | Oyola et al. |
| 2014/0107420 | A1* | 4/2014 | Konno ..................... A61B 1/31 600/114 |
| 2015/0313449 | A1* | 11/2015 | Stand ................... A61B 1/0055 604/525 |

* cited by examiner

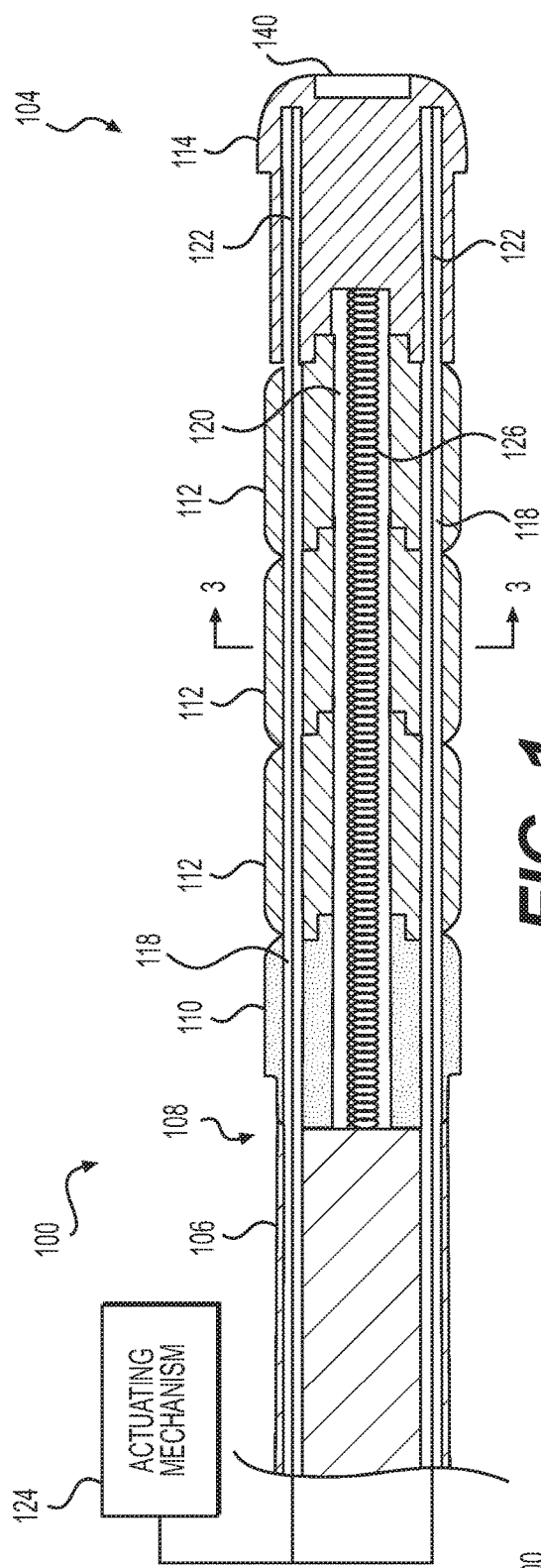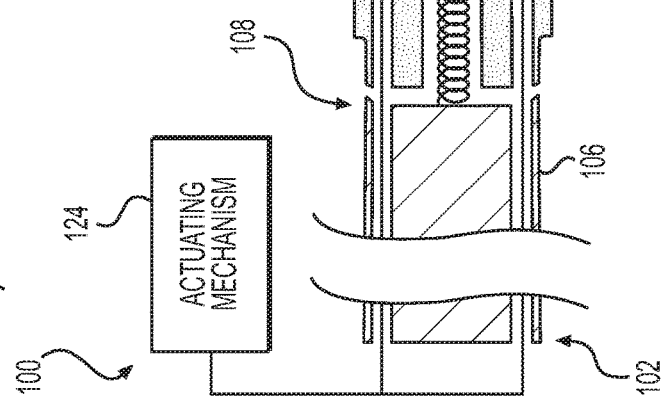

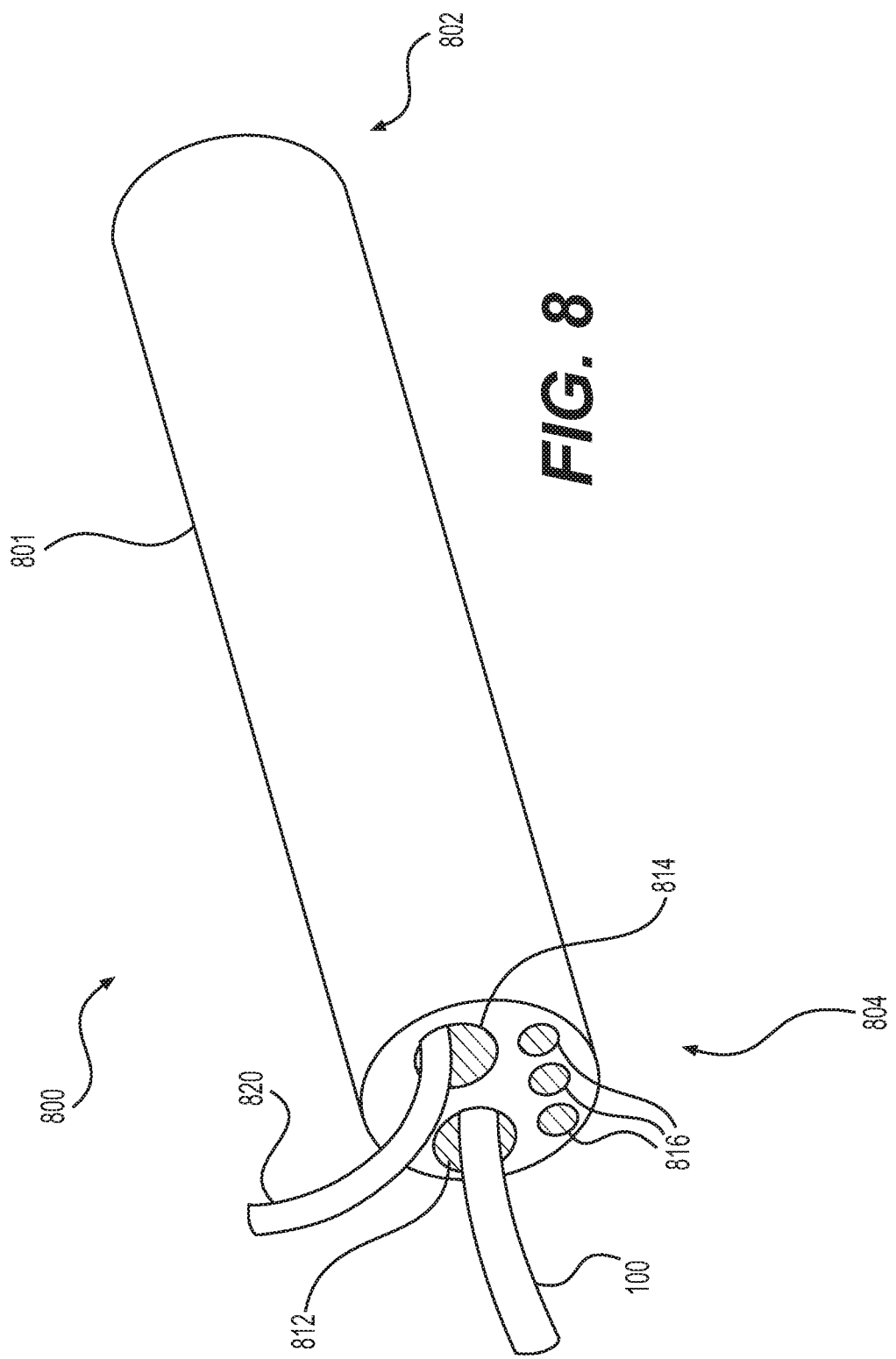

TISSUE DEFLECTING DEVICES AND RELATED METHODS OF USE

CROSS-REFERENCE TO RELATED APPLICATION(S)

This patent application claims the benefit under 35 U.S.C. § 119 to U.S. Provisional Patent Application No. 62/506,289, filed on May 15, 2017, the entirety of which is incorporated herein by reference.

TECHNICAL FIELD

Examples of the present disclosure relate to tissue deflecting devices, and related methods of use.

BACKGROUND

Lesions or other undesirable tissue may form in internal organs or other tissue tracts within the body. Such undesirable tissue may irritate the surrounding tissue or, in more serious cases, may be cancerous. If lesions are not quickly removed, they can cause deterioration of the surrounding tissue and subsequent failure of the organ or tissue tract.

One method of removing the undesirable tissue is through a conventional open surgical procedure during which the undesirable tissue is cut away. Such an open surgical procedure, however, is highly invasive, expensive, relatively traumatic to the patient, and would be inappropriate for many situations where only a small amount of tissue, for example, a small lesion, needs to be removed.

For patients with lesions in their bowel, one current practice is to have a physician locate the lesion endoscopically, and mark the lesion with a dye. Then, during a separate visit, the physician attempts to locate the lesion via the dye laprascopically, and surgically remove it. However, this initial marking does not always accurately reflect the location of the lesion.

SUMMARY

In one aspect, the present disclosure is directed to a medical device having a plurality of links reciprocally movable between a loose configuration having a first rigidity and a compact configuration having a second rigidity greater than the first rigidity, wherein application of a force to a distalmost link of the plurality of links when the plurality of links are in the loose configuration causes the plurality of links to change orientation relative to one another, and application of the force to the distalmost link when the plurality of links are in the compact configuration does not cause the plurality of links to change orientation relative to one another.

Adjacent links of the plurality of links may touch one another in the compact configuration, and have a space between one another in the loose configuration. The medical device may have a greater length when in the loose configuration than when in the compact configuration. Adjacent links of the plurality of links may be nested in the compact configuration, and may not be nested in the loose configuration. Application of a second force to an outer surface of any of the plurality of links when the plurality of links are in the loose configuration causes the plurality of links to change orientation relative to one another, and application of the second force to the outer surface of any of the plurality of links when the plurality of links are in the compact configuration does not cause the plurality of links to change orientation relative to one another. Central axes of the plurality of links may be coaxial in the compact configuration. A distal end of the distalmost link may be devoid of any openings through which a tool could pass through, and a circumferential side surface of the distalmost link may be devoid of any openings through which a tool could pass through. In the compact configuration, a tool lumen may extend through each of the plurality of links and has an opening in the distalmost link to permit a tool to extend through the tool lumen and distally out of the opening. The distalmost link may include an atraumatic distal tip. The medical device may include an actuation lumen extending at least partially through each of the plurality of links, an actuation member extending through the actuation lumen, and an actuating mechanism configured to apply a proximally directed force to the actuation member to move the plurality of links from the loose configuration to the compact configuration, wherein release of the proximally directed force causes the plurality of links to move from the compact configuration to the loose configuration. The medical device may include a spring lumen extending at least partially through each of the plurality of links, and a spring extending through the spring lumen, wherein the spring is biased into a longitudinally extended configuration that maintains the plurality of links in the loose configuration. The spring lumen and the spring may extend only partially through the distalmost link of the plurality of links. The medical device may include a light emitting component in the distalmost link of the plurality of links. The distalmost link may include a transparent material through which the light emitting component emits light. A proximal end of the distalmost link may include a recess, and a distal end of a proximally adjacent link to the distalmost link may include a tip corresponding in shape to the recess, wherein the recess and the tip prevent radial movement between the distalmost link and the proximally adjacent link in the compact configuration.

In another aspect, the present disclosure is directed to a medical device having a plurality of links reciprocally movable between a loose configuration and a compact configuration, the plurality of links being fixed relative to one another when in the compact configuration, and movable relative to one another in the loose configuration.

Application of a force to a distalmost link of the plurality of links when the plurality of links are in the loose configuration causes the plurality of links to change orientation relative to one another, and application of the force to the distalmost link when the plurality of links are in the compact configuration does not cause the plurality of links to change orientation relative to one another. The medical device may have a greater length when in the loose configuration than when in the compact configuration.

In yet another aspect, the present disclosure is directed to a method for removing a lesion from a tract of a patient. The method may include positioning an insertion tube within the tract, extending a medical device having a plurality of links through the insertion tube while the plurality of links are in a loose configuration, transitioning the plurality of links from the loose configuration to a compact configuration, extending the medical device through an opening at a distal end of the insertion tube and distally away from the insertion tube to push the tract toward a tissue wall of the patient, and removing the lesion from the tract via an incision through the tissue wall.

The method may include activating a light emitting component at a distal end of the medical device to illuminate the lesion, wherein removing the lesion includes cutting the illuminated lesion.

BRIEF DESCRIPTION OF THE DRAWINGS

The accompanying drawings, which are incorporated in and constitute a part of this specification, illustrate various examples and together with the description, serve to explain the principles of the disclosed examples.

FIG. 1 is a side cross-sectional view of a medical device in a first configuration, according to an example of the present disclosure.

FIG. 2 is a side cross-sectional view of the medical device of FIG. 1 in a second configuration.

FIG. 8 is a perspective view of a scope and a medical device according to an example of the present disclosure.

DETAILED DESCRIPTION

Figure 3:
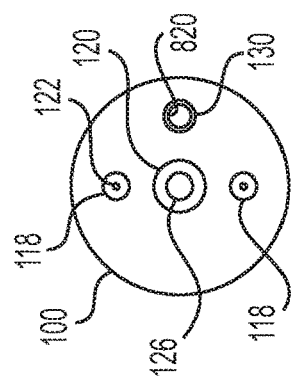
FIG. 3 is a cross-sectional view taken along line 3-3 of FIG. 1.

Reference will now be made in detail to examples of the present disclosure, which are illustrated in the accompanying drawings. Wherever possible, the same reference numbers will be used throughout the drawings to refer to the same or like parts or components. The term "distal" refers to the direction that is away from the user or operator and into the patient's body. By contrast, the term "proximal" refers to the direction that is closer to the user or operator and away from the patient's body.

Examples of the present disclosure are directed to medical devices configured to deflect tissue to facilitate various medical procedures. The disclosed medical devices may be able to pass through a scope in a loose, flexible state, and extend beyond the distal end of the scope in a rigid state to deflect tissue from one location to another.

A medical device 100 is shown in a first, compact configuration in FIG. 1, and in a second, loose configuration in FIG. 2. Medical device 100 may be reciprocally movable between the first and second configurations, and also may be configured to extend through an endoscopic device, e.g., scope 800 described below with reference to FIG. 8. Medical device 100 may extend from a proximal end 102 (shown only in FIG. 2) toward a distal end 104. Medical device 100 may include a catheter 106 at proximal end 102, and a plurality of links that extend distally from a distal end 108 of catheter 106.

A first link 110 may be adjacent to distal end 108 of catheter 106. A plurality of second links 112 may extend distally from first link 110, and a third link 114 may extend distally from a distalmost second link 112. While three second links 112 are shown with reference to FIGS. 1 and 2, any other suitable number of second links 112 may be used, including, but not limited to one, two, four, eight, or more second links 112. Referring to FIG. 1, medical device 100 may include one or more actuation lumens 118, and a spring lumen 120. An actuation member 122 may extend through each of the actuation lumens 118, and may be coupled at their proximal ends to an actuating mechanism 124. A spring 126, or another suitable compressible member, may extend through spring lumen 120. In one example, spring 126 may be biased into a longitudinally extended configuration as shown in FIG. 2, which may urge the links of medical device 100 to the loose configuration of FIG. 2. Alternatively, instead of a single spring 126, separate, and shorter, springs or compressible members may couple adjacent links to one another.

Actuation members 122 may be wires, cables, rods, tubes, or any other suitable members configured to receive a proximally directed pulling force from actuating mechanism 124. Actuating mechanism 124 may include any suitable features configured to apply the proximally directed pulling force to actuation members 122, including, for example, one or more of gears, pulleys, wheels, shafts, and the like. Actuating mechanism 124 may be motorized and/or electrically driven in some examples, and/or may be actuated manually by the operator.

Medical device 100 also may include one or more light emitting components 140 at distal end 104. The light emitting components may be, e.g., LEDs, optical fibers, or the like. Light emitting components 140 also may be located in other portions of medical device 100, including, e.g., side surfaces of catheter 106, first link 110, second link 112, and third link 114.

When medical device 100 is in the loose configuration of FIG. 2, a proximally directed force may be applied by actuating device 124 to actuation members 122. In response to the proximally directed force, medical device 100 may move from the loose configuration of FIG. 2 to the compact configuration of FIG. 1 by compressing spring 126. In some examples, the proximally directed force must be maintained by actuating mechanism 124 to keep medical device 100 in the compact configuration. Medical device 100 may be transitioned back to the loose configuration by releasing the proximally directed force acting on actuation members 122, allowing spring 126 to expand longitudinally and force the links of medical device 100 away from one another. The links and actuation members of medical device 100 may be slack in the loose configuration.

The loose configuration (FIG. 2) of medical device 100 may help medical device 100 navigate through tortuous pathways of the body, or to navigate through the tortuous path of an artificial lumen (e.g., lumen 812 shown in FIG. 8) after a scope is extended through a tortuous pathway of the body. Medical device 100 may be used to deflect tissue or other bodily structures while disposed in its rigid, compact state (FIG. 1).

In the loose configuration, the various links of medical device 100 may be spaced apart from adjacent links, and may loosely ride along actuation members 122. However, in the compact configuration, the links of medical device may directly contact one another in a nested manner. In the loose configuration, the links of medical device 100 may change orientation relative to one another in response to an outside force acting on one or more of the links (e.g., third link 114). In the compact configuration, the links of medical device 100 may not change orientation relative to one another in response to an outside force (such as the same outside force (magnitude and direction) mentioned in the prior sentence) acting on one or more of the links (e.g., third link 114). That is, in the compact configuration, the plurality of links may form a rigid pushing member that is substantially straight, and which remains substantially straight when contacting tissue or other objects. Thus, distal end 104 of medical device 100 comprising the plurality of links may have a greater rigidity in the compact configuration than while in the loose configuration. Additionally, the plurality of links may be fixed relative to one another when in the compact configuration, and may be movable relative to one another in the loose configuration. Medical device 100 also may have a greater length in the loose configuration than when in the compact configuration, as gaps between adjacent links present in the loose configuration may be closed after the transition to the compact state.

A cross-sectional view of medical device 100 is shown in FIG. 3, which shows two actuation lumens 118 that are disposed on opposite sides of medical device 100. That is, the two actuation lumens 118 may be separated by an arc length of about 180 degrees, although other spacing is also contemplated. While two actuation lumens 118 are shown, any other suitable number of actuation lumens, e.g., three, four, or more, may be utilized. The actuation lumens 118 may be spaced apart from one another at even or uneven intervals, and each may receive an actuation member 122. Spring lumen 120 may be disposed radially inward of actuation lumens 118 as shown, or may be disposed in a different configuration, such as radially aligned or radially outward of the actuation lumens 118. In the example shown, spring lumen 120 is in the radial center of medical device 100. In some examples, medical device 100 may include a tool lumen 130 extending therethrough. The tool lumen 130 may be sized to accommodate various medical tools 820, such as, e.g., a cutting wire, an injection needle, a needle knife, a snare, forceps, a grasper, an ablative or non-ablative energy delivery device, a cryo-tool configured to reduce the temperature of tissue, or other therapeutic or diagnostic devices. The tool lumen 130 may extend from proximal end 102 to an opening at distal end 104. Tool lumen 130 may permit a tool to be inserted, e.g., at proximal end 102, and delivered through an opening at the distal end 104 of medical device 100. Any suitable number of tool lumens 130, e.g., two or more, may be included in medical device 100. However, in other examples, medical device 100 may not include any tool lumen and may not be configured to pass any tool through its distal end.

Figure 4:
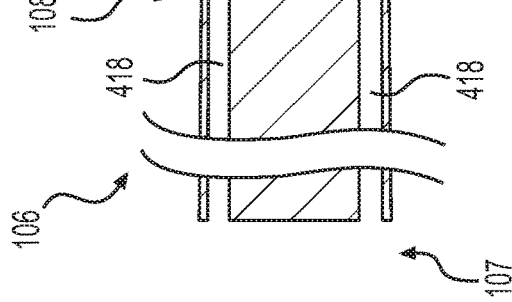
FIG. 4 is a side cross-sectional view of a catheter according to an example of the present disclosure.

Catheter 106, shown separately in FIG. 4, may extend from a proximal end 107 to distal end 108. Catheter 106 may be a flexible member configured to navigate through tortuous anatomy and may include any suitable material including, e.g., polymers, metals, and/or metal alloys. Catheter 106 may include one or more actuation lumens 418, and a tool lumen (not shown) that form portions of actuation lumen 118 and tool lumen 130, respectively. Spring 126 may be coupled to a distally-facing surface at distal end 108 of catheter 106.

Figure 5:
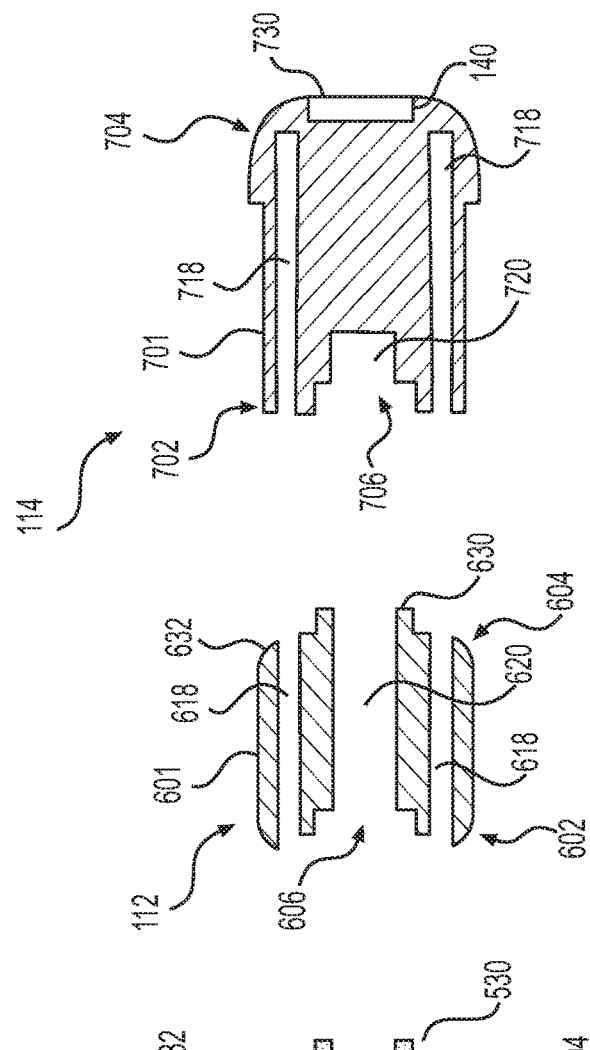
FIG. 5 is a side cross-sectional view of a first link according to an example of the present disclosure.

First link 110, shown separately in FIG. 5, may have a body 501 that extends from a proximal end 502 to a distal end 504. Proximal end 502 may be adjacent to distal end 108 of catheter 106. First link 110 may be substantially rigid and may include any suitable material including, e.g., polymers, metals, and/or metal alloys. First link 110 may include one or more actuation lumens 518, a spring lumen 520, and a tool lumen (not shown) that form portions of actuation lumens 118, spring lumen 120, and tool lumen 130, respectively. First link 110 also may include a tip 530 extending distally from distal end 504. The tip 530 may have a smaller radial dimension or diameter than body 501. Spring lumen 520 and/or an associated tool lumen may extend through the tip 530. First link 110 also may include a shoulder 532 through which actuation lumens 518 extend. It is also contemplated that one or more of spring lumen 520 and/or an associated tool lumen may extend through shoulder 532 instead of tip 530. First link 110 may be generally cylindrical in shape, although other suitable shapes are also contemplated.

Figure 6:
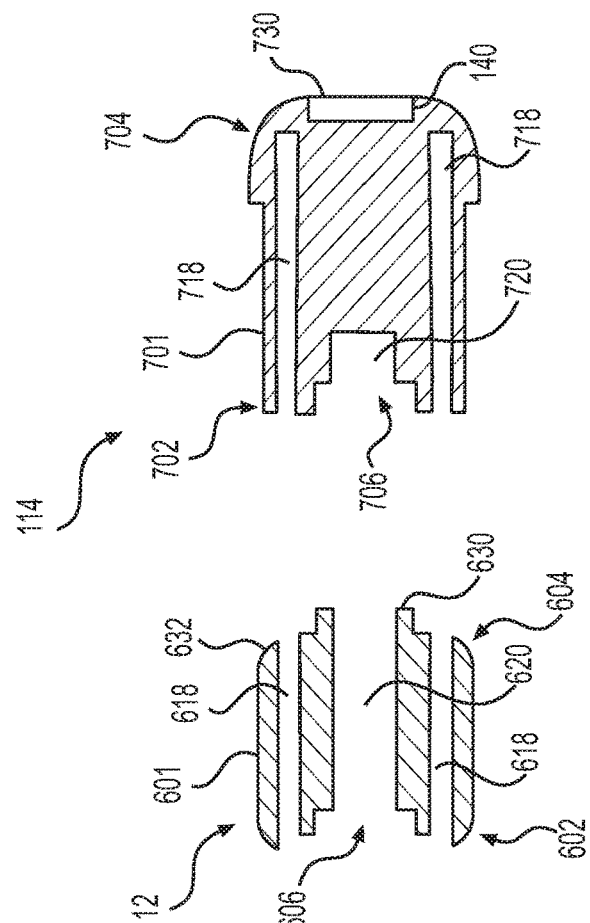
FIG. 6 is a side cross-sectional view of a second link according to an example of the present disclosure.

Second link 112, shown separately in FIG. 6, may have a body 601 that extends from a proximal end 602 to a distal end 604. Proximal end 602 may be adjacent to either distal end 504 of first link 110, or to a distal end 604 of another second link 112. A recess 606 may be disposed at proximal end 602. Recess 606 may be sized to receive tip 530 of first link 110, or a tip 630 (described below) of another second link 112. Second link 112 may be formed of substantially the same materials as first link 110. Second link 112 may include one or more actuation lumens 618, a spring lumen 620, and a tool lumen (not shown) that form portions of actuation lumen 118, spring lumen 120, and tool lumen 130, respectively. Second link 112 also may include a tip 630 extending distally from distal end 604. The tip 630 may have a smaller radial dimension or diameter than body 601. Spring lumen 620 and/or an associated tool lumen may extend through the tip 630. Second link 112 also may include a shoulder 632 through which actuation lumens 618 extend. It is also contemplated that one or more of spring lumen 620 and/or an associated tool lumen may extend through shoulder 632 instead of tip 630. Second link 112 may be generally cylindrical in shape, although other suitable shapes are also contemplated.

Figure 7:
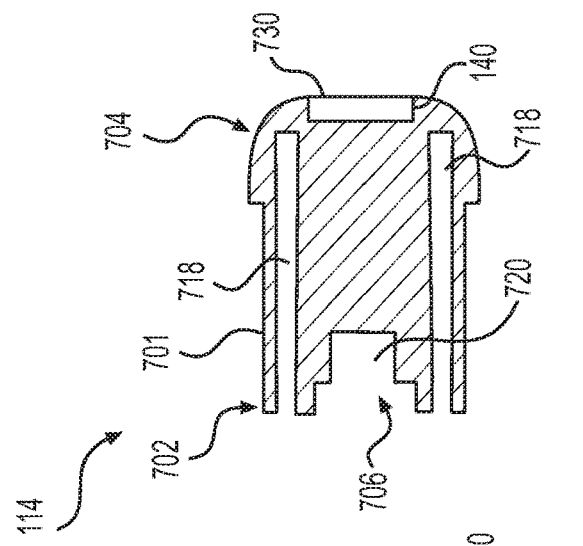
FIG. 7 is a side cross-sectional view of a third link according to an example of the present disclosure.

Third link 114, shown separately in FIG. 7, may have a body 701 that extends from a proximal end 702 to a distal end 704. Proximal end 702 may be adjacent to a distal end 604 of a second link 112. A recess 706 may be disposed at proximal end 702. Recess 706 may be sized to receive tip 630 of a second link 112. Third link 114 may be formed of substantially the same materials as first link 110 and second link 112. Third link 114 may include one or more actuation lumens 718, a spring lumen 720, and a tool lumen (not shown) that form portions of actuation lumen 118, spring lumen 120, and tool lumen 130, respectively. Actuation lumen 718 and spring lumen 720 may form the distalmost portions of actuation lumen 118 and spring lumen 120, respectively. Actuation lumen 718 and spring lumen 720 extend only partially through third link 114 in some examples. The distal ends of actuation members 122 may be coupled to a surface, e.g., a proximally-facing surface at the distal end of actuation lumen 718, and spring 126 may be coupled to a proximally-facing surface at the distal end of spring lumen 720. Third link 114 may include an atraumatic tip 730. The tip 730 may have a larger radial dimension or diameter than a remaining portion of body 701.

The atraumatic tip 730 may be configured to reduce or prevent damage to tissue that is contacted by the atraumatic tip 730. For example, the atraumatic tip 730 may include a polymer material having a relatively small durometer or hardness. In other examples, atraumatic tip 730 may include a ball tip or any other features, such as rounded edges, configured to reduce damage to tissue that contacts the tip. Third link 114 may be generally cylindrical in shape, although other suitable shapes are also contemplated. The one or more light emitting components 140 of medical device 100 may be located at distal end 704 of third link 114. The light emitting components may be embedded within third link 114 in some examples, and at least a portion of third link 114 may be formed from a transparent material.

In some examples, a tool lumen may extend through third link 114, allowing tools to be passed through the distal end 104 of the medical device 100. However, in other examples, third link 114 may be completely closed at distal end 704 such that no tool may be passed through the distal end 104 of medical device 100. In such examples, no tool may be passed through the distalmost surface of third link 114, or through any circumferential side surface of third link 114. That is, both the distalmost surface and the circumferential side surface of the third link 114 may be devoid of any opening through which a tool could pass through. In one example, third link 114 includes openings only at proximal end 702 for actuation lumen 718 and spring lumen 720. However, those openings do not permit a tool to pass from proximal end 702, through the third link 114, and out of a distal surface or a circumferential side surface of the third link 114. Instead, actuation lumen 718 and spring lumen 720 each terminate within the third link 114. A closed distal end may be particularly beneficial in applications where medical device 100 is used only as a pushing device, as the smooth distal pushing surface and lack of openings at the distal end of medical device 100 may help prevent tissue from inadvertently snagging at the distal end of medical device 100.

The actuation and tool lumens of catheter 106, first link 110, second link 112, and third link 114 may be aligned with one another to form actuation lumens 118 and tool lumen 130 when medical device 100 is in the compact configuration. Similarly, the spring lumens of first link 110, second link 112, and third link 114 may be aligned with one another to form spring lumen 126 when medical device 100 is in the compact configuration. Additionally, the recesses and tips of the various links may help interlock adjacent links and prevent radial movement between adjacent links when medical device 100 is in the compact configuration.

One or more portions of medical device 100 may include a lubricious coating to reduce friction between the medical device 100 and contacted tissue. Any suitable lubricious coating may be utilized, including water soluble, biocompatible compounds that impart lubricity to the surface of otherwise non-lubricious materials. One exemplary class of hydrophilic coatings includes hydrogels, which swell in an aqueous environment, and are capable of manifesting lubricity while in a wet or hydrated state. When hydrated, these substances have low frictional forces in humoral fluids including saliva, digestive fluids and blood, as well as in saline solution and water. Exemplary hydrogels include polyethylene oxides, optionally linked to the substrate surface by urethane or ureido linkages or interpolymerized with poly(meth)acrylate polymers or copolymers, copolymers of maleic anhydride, (meth)acryl amide polymers and copolymers, (meth)acrylic acid copolymers, polyurethanes, poly (vinyl pyrrolidone) and blends or interpolymers with polyurethanes, polysaccharides, and mixtures thereof.

Scope 800 is shown in FIG. 8. Scope 800 may include a flexible shaft 801 that extends from a proximal end 802 to a distal end 804. Shaft 801 may be configured to navigate tortuous anatomy within a patient. In some examples, shaft 801 may be uniformly flexible, or may include portions having varied flexibility. For example, distal end 804 of shaft 801 may be more flexible than proximal end 802. Scope 800 may be any suitable medical scope, such as, e.g., an endoscope, a ureteroscope, a colonoscope, a hysteroscope, a bronchoscope, or a cystoscope. Shaft 801 may be directly inserted into the body of a patient or may be extended over a guidewire using one or more lumens. Shaft 801 also may be inserted into a laparoscopic port, a single incision port, an over-tube, a bouché, or any other suitable member.

Shaft 801 may include multiple lumens extending therethrough, for example, a lumen 812, a lumen 814, and additional lumens 816. Although the depicted embodiment of scope 800 has five lumens, any other suitable number of lumens is also contemplated. Lumens 812, 814, and 816 may have any suitable length, size, cross-sectional area, shape, and/or configuration, and may extend along at least a portion of the length of shaft 801. In one example, one or more of the lumens may extend substantially along the entire length of shaft 801.

As shown in FIG. 8, each of lumens 812 and 814 may be configured to accommodate one or more tools extending therethrough. For example, medical device 100 may extend through lumen 812, while a second tool 820 may extend through lumen 814. The opening of lumen 812 at distal end 804 may lie in a plane, and medical device 100 may be configured to extend distally away from the distal end 804 along a trajectory that is substantially perpendicular to the plane of the opening.

At least one lumen 816 may be configured to accommodate any suitable visual device. For example, a lumen 816 may be configured to contain a visual device allowing a user to view an area adjacent to distal end 804 of scope 800, including areas distal to distal end 804. The visual device may be built into scope 800, and include one or more of a light source, lens, fiber optics, and/or any suitable electronic vision components known in the art, etc., to view a work site within a patient's body lumen. In another example, a separate imaging device may be utilized. It is also contemplated that lumens 816 may be utilized for any other suitable purpose, such as, e.g., irrigation, aspiration, suction, delivery of additional tools, delivery of therapeutics, or as a guiding lumen which is used to guide shaft 801 over a guidewire.

The scope 800 may not be able to push tissue along a trajectory perpendicular to a longitudinal axis of the scope in some instances. However, when the medical device 100 is passed through the scope 800, the scope 800 may act as an anchor, and the medical device 100 is able to push off scope 800 and move tissue along the trajectory perpendicular to the longitudinal axis of scope 800.

Devices of the present disclosure, e.g., medical device 100, may be used to move tissue from one location to another. For example, medical device 100 may be used to move a loop of a patient's bowel toward the peritoneal wall to allow access for a variety of therapies, and/or for diagnostic purposes. Medical device 100 may be used to move contacted tissue toward other tissue. There are many potential uses of medical device 100. The following uses are only exemplary.

Figure 9:
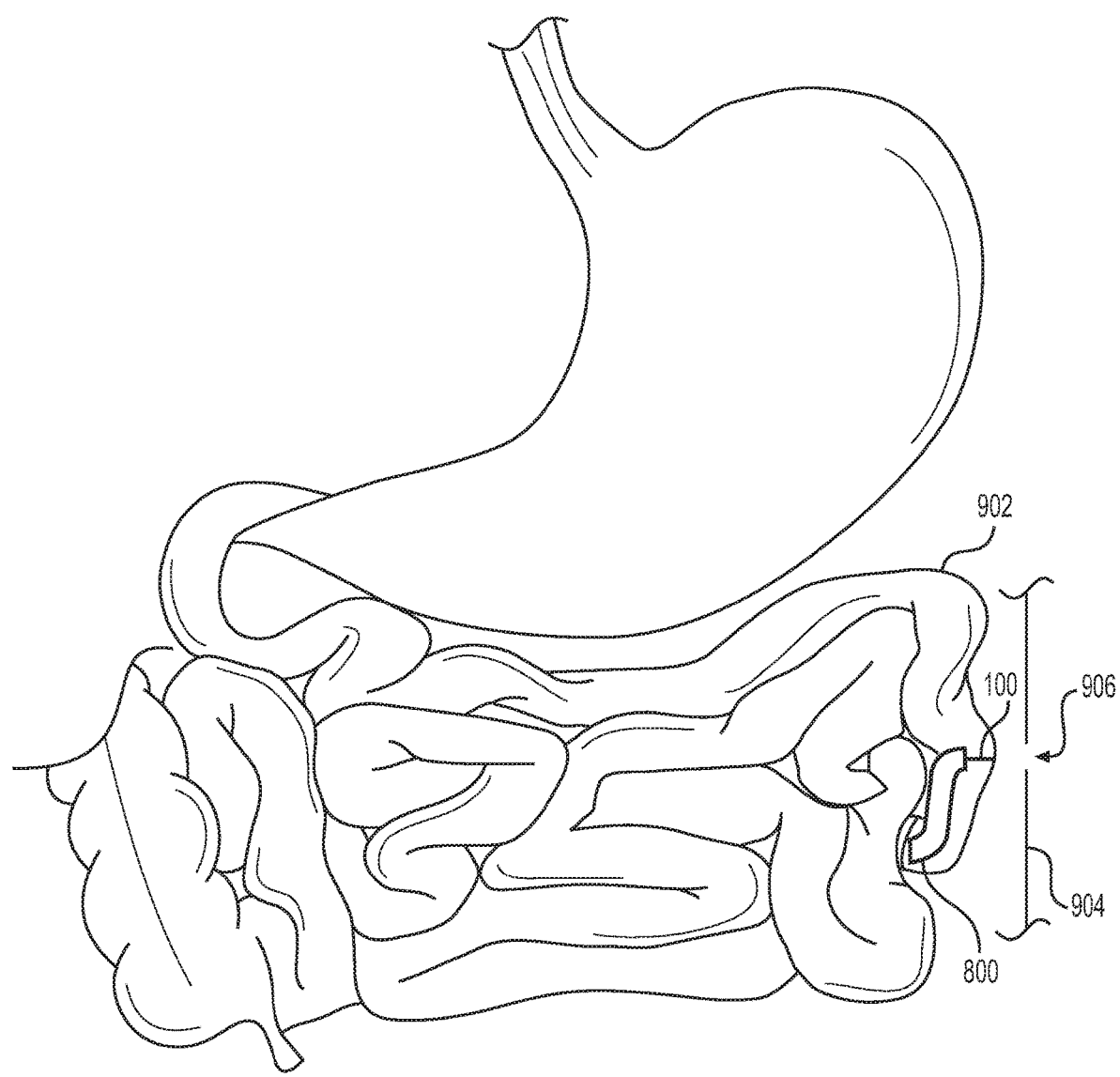
FIG. 9 is a schematic view of a surgical procedure according to an example of the present disclosure.

Medical device 100 may assist a physician during removal of lesions in the intestine/bowel, and/or during placement of various feeding or drainage tubes (e.g., jejunal feeding tubes or J-tubes) in the abdomen. FIG. 9 depicts a schematic view of a stomach and the surrounding gastrointestinal structures. An esophagus is shown leading to a stomach. The stomach includes a fundus at its proximal end and an antrum at its distal end. The antrum feeds into the pylorus, which attaches to the duodenum at the proximal region of the small intestine. The middle region of the small-intestine, positioned distally of the duodenum, is the jejunum.

FIG. 9 shows scope 800 and medical device 100 disposed within the intestinal tract 902. More specifically, medical device 100 is shown extending distally from the distal end of scope 800 to push a portion the intestinal tract 902 toward peritoneal wall 904. An incision 906 may be made in the peritoneal wall 904.

Figure 10:
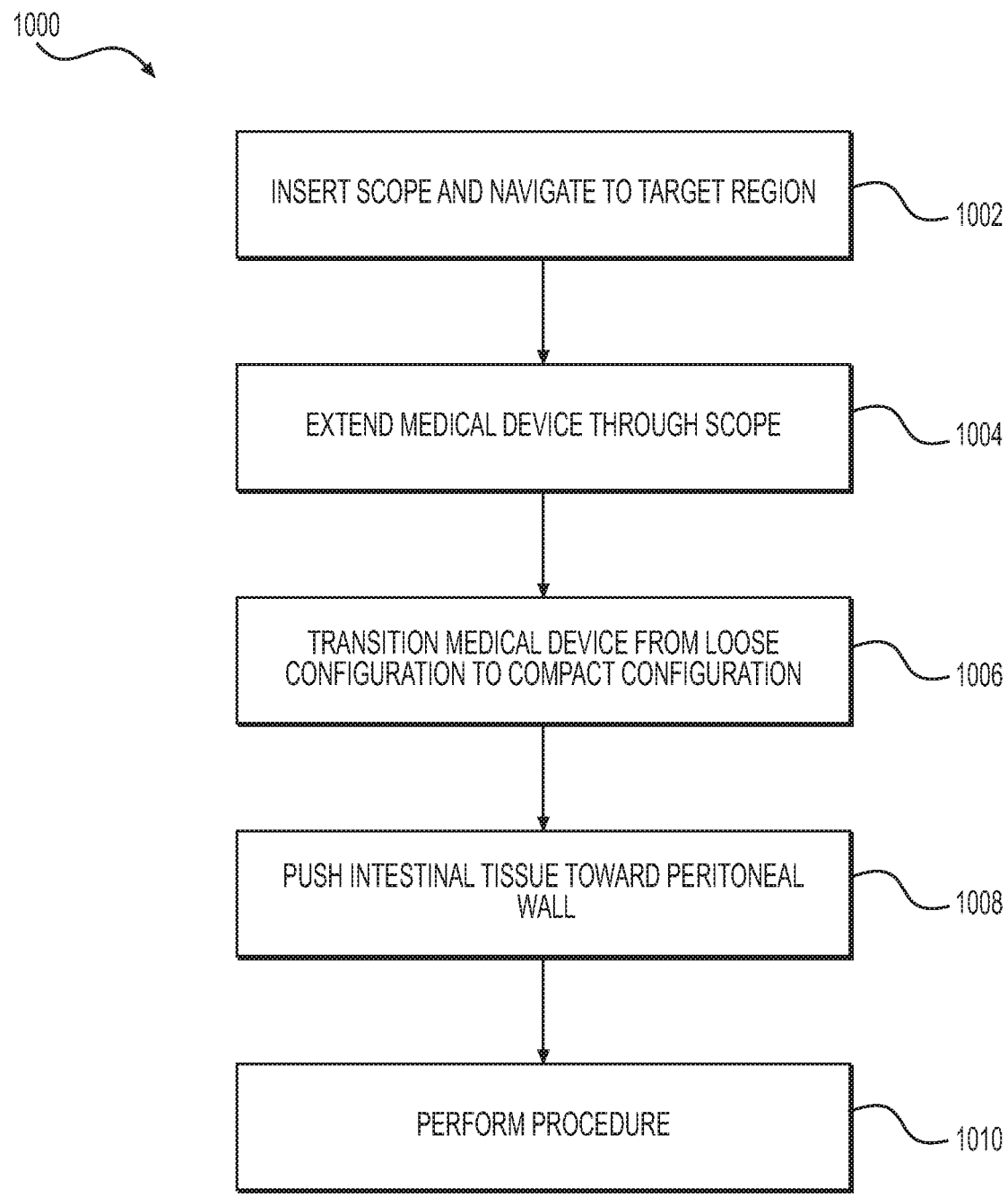
FIG. 10 is a flow chart of a method of performing the surgical procedure shown in FIG. 9.

A method 1000 is shown in FIG. 10, which may be carried out in the environment shown in FIG. 9. The method 1000 may begin at step 1002, where scope 800 may be inserted into the body and navigated to a target region. For example, scope 800 may be inserted into the body through a natural anatomic opening, such as, for example, the mouth, anus, nose, or vagina. Alternatively, scope 800 may be inserted into the body through an incision. An operator may navigate scope 800 from the point of insertion to a target region (e.g., work site) within the body by traversing a body channel, such as, e.g., the intestinal tract 902. Navigation of scope 800 may be facilitated by e.g., visualization via the visual device in lumen 816, or by other suitable tracking and guidance mechanisms.

Once distal end 804 of scope 800 is adjacent or otherwise proximate to the target region, medical device 100 may be inserted through a port of the scope 800 while in the loose configuration shown in FIG. 2 (step 1004). Medical device 100 then may be pushed toward the distal end 804 of scope 800. Once medical device 100 is at distal end 804 of scope 800, the method may proceed to step 1006, where actuation members 122 may be pulled proximally by actuating mechanism 124 to transition medical device from the loose configuration of FIG. 2 to the rigid and compact configuration of FIG. 1.

Once medical device 100 is in the rigid and compact configuration, it may be extended distally from distal end 804 to contact a portion of the intestinal tract 902. The contacted portion of the intestinal tract 902 may be a lesion to be surgically removed, or may be a site identified for placement of a tube such as, e.g., a jejunal tube. Medical device 100 may be used to push the contacted tissue toward peritoneal wall 904 (step 1008), and more particularly toward an incision 906 made through the peritoneal wall 904. Pushing the intestinal tract 902 toward the peritoneal wall 904 may assist with visualization of the target region from a laparoscopic device positioned external to the intestinal tract 902.

After the intestinal tract 902 is pushed toward the peritoneal wall 904, method 1000 may proceed to step 1010 where a procedure may be performed at or adjacent to the contacted tissue/target region. In a first example, the procedure may include removing tissue from the intestinal tract 902 (e.g., a lesion) with a laparoscopic tool (e.g., blade, cutting wire, scissors, cryoprobe, or the like) inserted through incision 906. The medical device 100 can improve laparoscopic lesion removal by allowing for a smaller incision and improved visualization of the lesion. In some examples, light emitting component 140 may be used to illuminate a lesion, and the laparoscopic tool may be used to cut the illuminated lesion.

Alternatively, at step 1010, the procedure may include inserting a feeding tube (e.g., a jejunal tube) into the patient. In this example, the contacted surface tissue that is pushed toward incision 906 may be a site identified for placement of the jejunal tube. The contacted and pushed tissue may be visualized via, e.g., the laparoscope, and an incision may be created through the intestinal tract 902 at or proximate to the contacted tissue via one or more tools passed through the laparoscope or otherwise passed through the incision 906. A light source coupled to either medical device 100 (e.g., light emitting component 140) or scope 800 may facilitate the visualization by highlighting the contacted tissue to be cut. Alternatively, a needle may be passed through the medical device 100 or scope 800 to make an incision from within intestinal tract 902. After making the incision, the needle could be used as a guide over which a tissue expanding device could move. The tissue expanding device may be configured to enlarge the incision made by the needle. The jejunal tube may be passed through the incision 906 in the peritoneal wall 904 and through the incision made in the intestinal tract 902. The jejunal tube may be secured in both the peritoneal wall 904 and the intestinal tract 902 by any suitable mechanism, and at least a portion of intestinal tract 902 may be secured to the peritoneal wall 904 by, e.g., suturing.

Pushing the intestinal tract 902 closer to the peritoneal wall 904 can simplify jejunal tube insertion procedures by allowing the physician to better visualize the intestinal tract 902 from a vantage point outside of the intestinal tract 902, and by reducing the size of incision required to be made in the peritoneal wall 904. This may result in more accurate, less invasive, and lower cost jejunal tube insertions.

Figure 11:
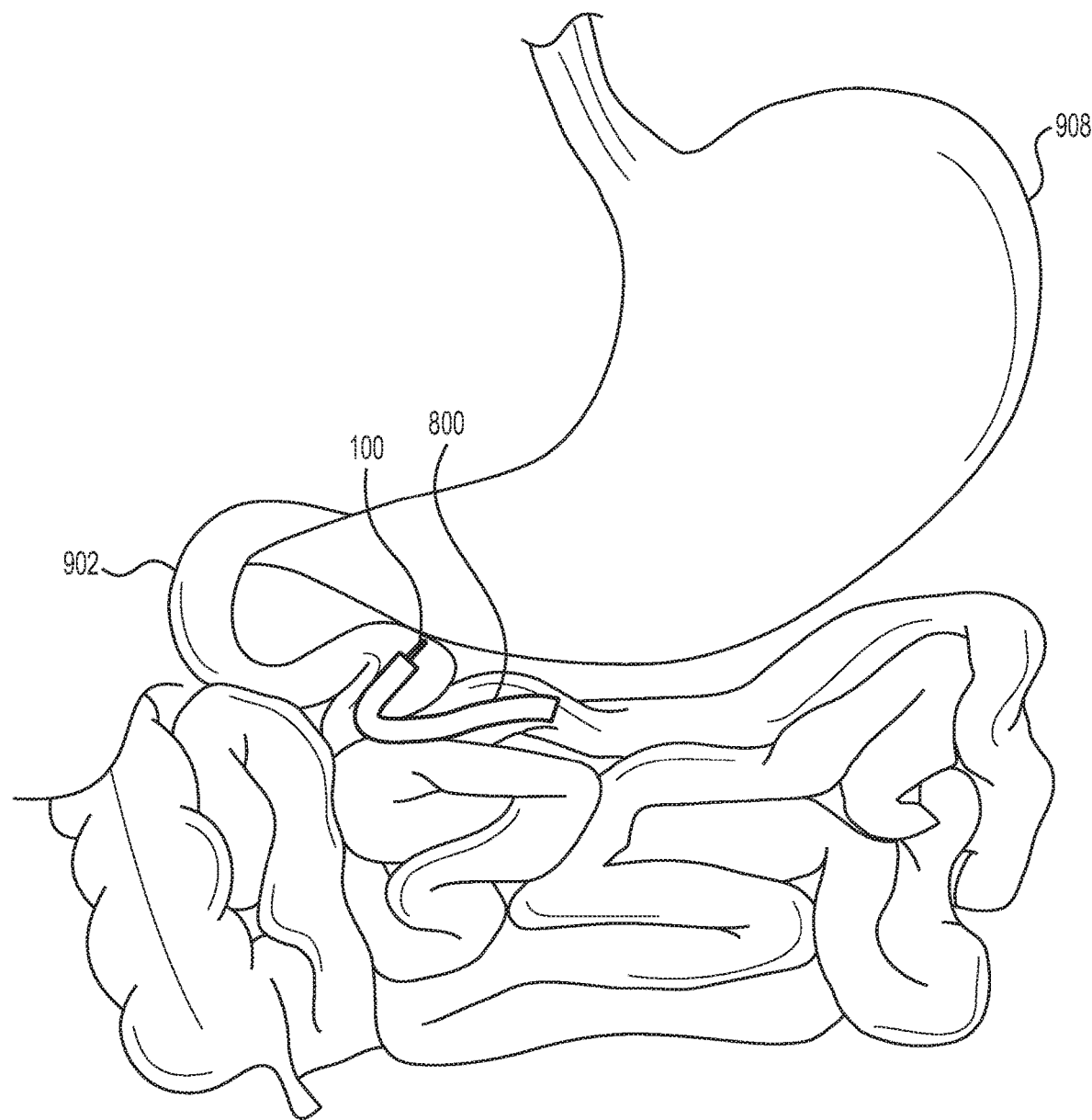
FIG. 11 is a schematic view of a surgical procedure according to an example of the present disclosure.

FIG. 11 depicts a schematic view of a stomach and the surrounding gastrointestinal structures. An esophagus is shown leading to a stomach. The stomach includes a fundus at its proximal end and an antrum at its distal end. The antrum feeds into the pylorus, which attaches to the duodenum at the proximal region of the small intestine. The middle region of the small-intestine, positioned distally of the duodenum, is the jejunum. FIG. 11 shows scope 800 and medical device 100 disposed within the intestinal tract 902. More specifically, medical device 100 is shown extending distally from the distal end 804 of scope 800 to push the intestinal tract 902 toward stomach 908.

Figure 12:
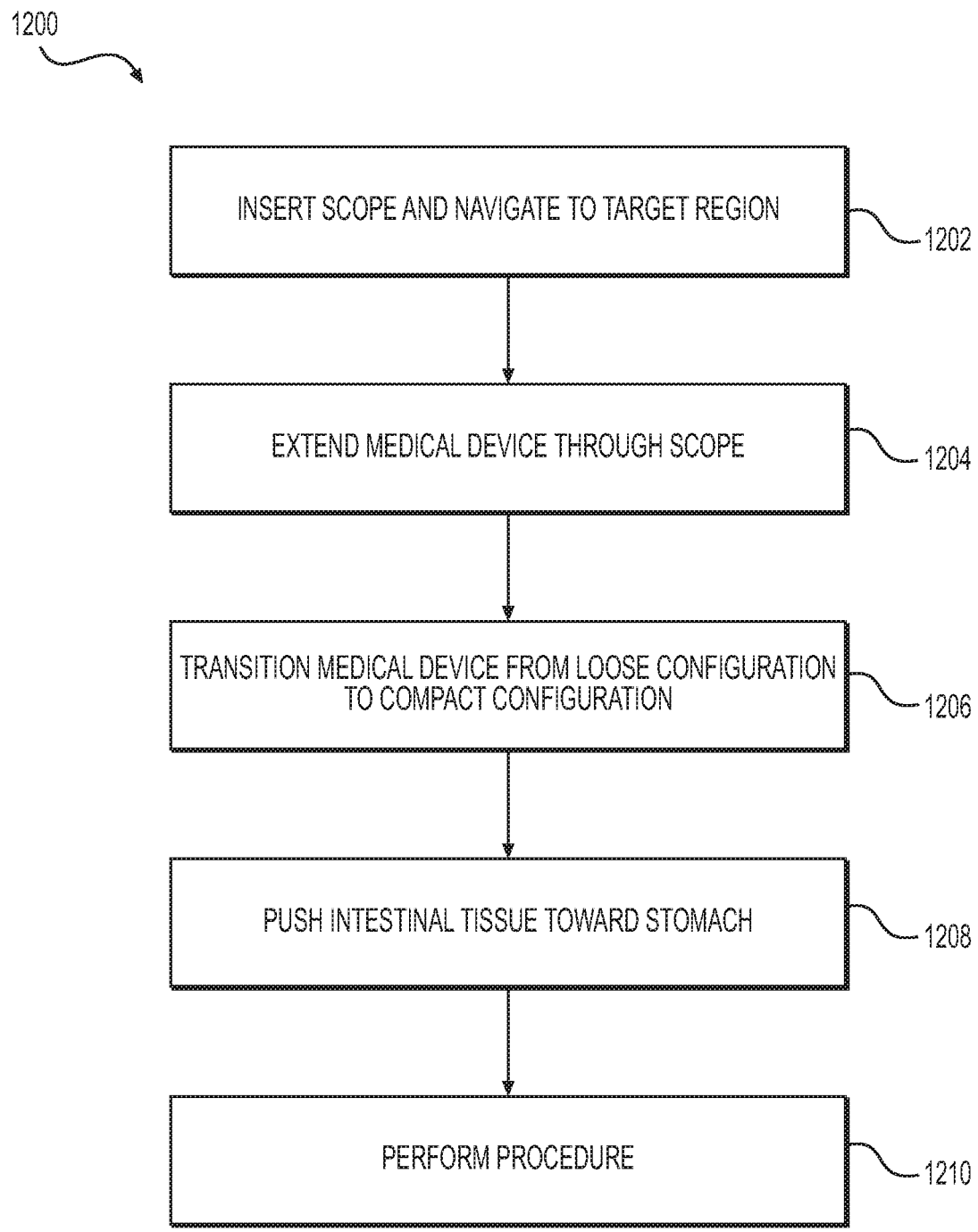
FIG. 12 is a flow chart of a method of performing the surgical procedure shown in FIG. 11.

A method 1200 is shown in FIG. 12, which may be carried out in the environment shown in FIG. 11. The method 1200 may begin at step 1202, where scope 800 may be inserted into the body and navigated to a target region in a substantially similar manner as set forth above with respect to step 1002 of FIG. 10.

Once distal end 804 of scope 800 is adjacent or otherwise proximate to the target region (e.g., a portion of the intestinal tract 902), medical device 100 may be inserted through a port of the scope 800 while in the loose configuration shown in FIG. 2 (step 1204). Medical device 100 then may be pushed toward the distal end 804 of scope 800. Once medical device 100 is at distal end 804 of scope 800, the method may proceed to step 1206, where actuation members 122 may be pulled proximally by actuating mechanism 124 to transition medical device from the loose configuration of FIG. 2 to the rigid and compact configuration of FIG. 1.

Once medical device 100 is in the rigid and compact configuration, it may be extended distally from distal end 804 to contact a portion of the intestinal tract 902. Medical device 100 may be used to push the contacted tissue toward stomach 908 (step 1208).

After the portion of the intestinal tract 902 is pushed toward the stomach 908, method 1200 may proceed to step 1210 where a procedure may be performed at or adjacent to the contacted tissue/target region. In one example, the procedure may include forming a fistula between the intestinal tract 902 and the stomach 908. In this example, a needle may be advanced through scope 800 or medical device 100 to make a first incision through the intestinal tract 902 and a second incision through the stomach 908. A stent or other implant may be delivered through the scope 800. In some examples, the stent may be a self-expanding, braided stent capable of allowing fluid and material flow from the stomach 908 to the intestinal tract 902 through the stent.

Method 1200 may help minimize the risk of unintentionally perforating other portions of the intestinal tract 902, which can occur when the incision for the anastomosis or fistula is started from within stomach 908.

Alternatively, medical device 100 may assist with locating the exact position for an internal incision in another natural orifice transluminal endoscopic surgery (NOTES) procedure.

Figure 13:
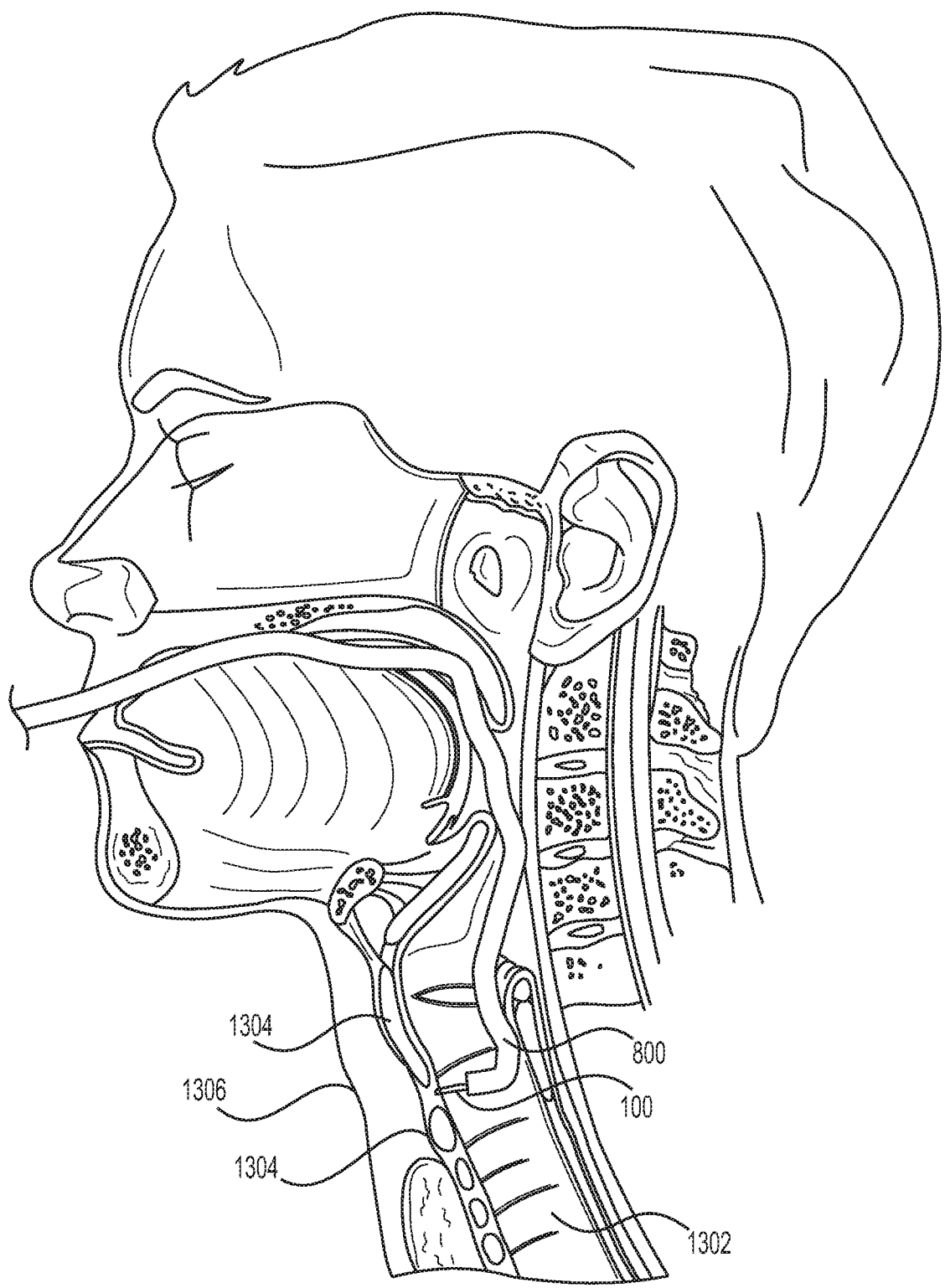
FIG. 13 is a schematic view of a surgical procedure according to an example of the present disclosure.

FIG. 13 shows scope 800 and medical device 100 disposed within the trachea 1302. More specifically, medical device 100 is shown extending distally from the distal end of scope 800 to perform a tracheotomy from within the trachea 1302.

Figure 14:
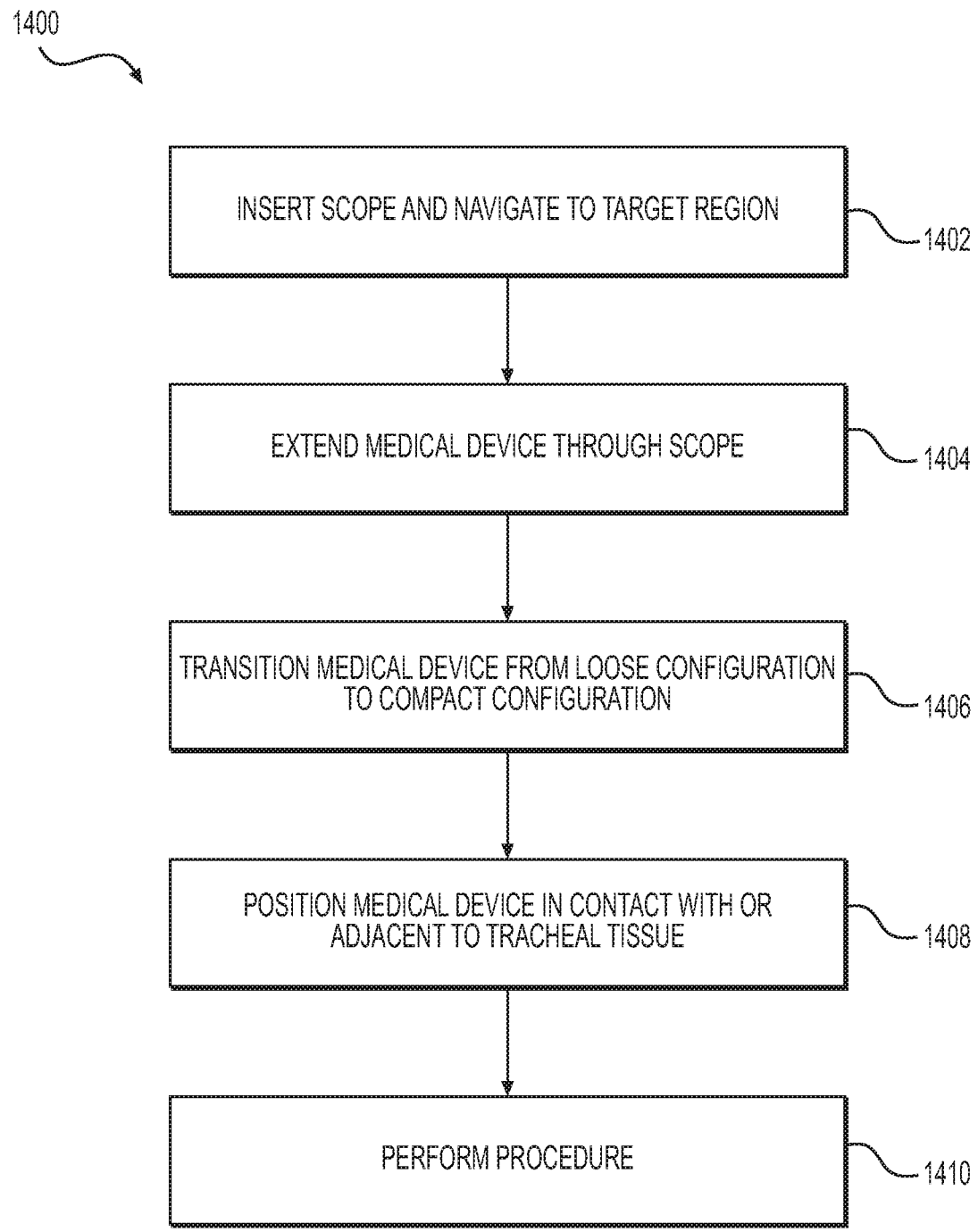
FIG. 14 is a flow chart of a method of performing the surgical procedure shown in FIG. 13.

A method 1400 is shown in FIG. 14, which may be carried out in the environment shown in FIG. 13. The method 1400 may begin at step 1402, where scope 800 may be inserted into the body through the mouth or nose, and navigated to a target region in a substantially similar manner as set forth above with respect to step 1002 of FIG. 10.

Once distal end 804 of scope 800 is adjacent or otherwise proximate to the target region (e.g., a region within trachea 1302), medical device 100 may be inserted through a port of the scope 800 while in the loose configuration shown in FIG. 2 (step 1404). Medical device 100 then may be pushed toward the distal end 804 of scope 800. Once medical device 100 is at distal end 804 of scope 800, the method may proceed to step 1406, where actuation members 122 may be pulled proximally by actuating mechanism 124 to transition medical device from the loose configuration of FIG. 2 to the rigid and compact configuration of FIG. 1.

Once medical device 100 is in the rigid and compact configuration, it may be extended distally from distal end 804 to contact tissue surrounding the trachea. In particular, medical device 100 may be placed in contact with tissue that is disposed between two adjacent cartilaginous portions 1304 of the trachea (step 1408).

After medical device 100 is placed between two cartilaginous portions 1304, method 1400 may proceed to step 1410 where a procedure may be performed at or adjacent to the contacted tissue/target region. In one example, the procedure may include passing a needle and wire through medical device 100 to form a channel from the trachea to the skin 1306 for placement of a tracheal tube. In this example, a needle may be advanced through medical device 100 to make an incision through tissue between two cartilaginous portions 1304 and through the skin 1306. The incision may be expanded by suitable mechanisms, such as, e.g., a tissue expander, and a tracheal tube may be subsequently inserted through the expanded opening.

Performing a tracheotomy with this method may help a physician more accurately identify sites for placing tracheal tubes, reduce the risk of crushing the trachea, and reduce the risk of obstructing airflow through the trachea and/or tracheal tube.

Those skilled in the art will understand that the medical devices set out above can be implemented in any suitable body lumen (e.g., blood vessels, the biliary tract, urological tract, gastrointestinal lumens, and the like) without departing from the scope of the disclosure as defined by the claims. In particular, constructional details, including manufacturing techniques and materials, are well within the understanding of those of skill in the art and have not been set out in any detail here. These and other modifications and variations are well within the scope of the present disclosure and can be envisioned and implemented by those of skill in the art.

Other examples of the present disclosure will be apparent to those skilled in the art from consideration of the specification and practice of the examples disclosed herein. It is intended that the specification and examples be considered as exemplary only, and departures in form and detail may be made without departing from the scope and spirit of the present disclosure as defined by the following claims.

What is claimed is:

1. A medical device, comprising:
an actuation member;
a plurality of links reciprocally movable over the actuation member between a loose configuration having a first rigidity and a compact configuration having a second rigidity greater than the first rigidity; and
a biasing mechanism disposed through a center lumen extending through the center of each of the plurality of links, wherein the biasing mechanism extends through the center lumen, is separated from an interior of the plurality of links when in the loose configuration and the compact configuration, and is biased into a longitudinally extended configuration that maintains the plurality of links in the loose configuration;
wherein application of a force to a distalmost link of the plurality of links when the plurality of links are in the loose configuration causes the plurality of links to change orientation relative to one another, and
application of the force to the distalmost link when the plurality of links are in the compact configuration does not cause the plurality of links to change orientation relative to one another, wherein the plurality of links are configured to translate along the actuation member and relative to one another when in the loose configuration.

2. The medical device of claim 1, wherein adjacent links of the plurality of links touch one another in the compact configuration, and have a space between one another in the loose configuration.

3. The medical device of claim 1, wherein the medical device has a greater length when in the loose configuration than when in the compact configuration.

4. The medical device of claim 1, wherein adjacent links of the plurality of links are nested in the compact configuration, and are not nested in the loose configuration.

5. The medical device of claim 1, wherein application of a second force to an outer surface of any of the plurality of links when the plurality of links are in the loose configuration causes the plurality of links to change orientation relative to one another, and application of the second force to the outer surface of any of the plurality of links when the plurality of links are in the compact configuration does not cause the plurality of links to change orientation relative to one another.

6. The medical device of claim 1, wherein the plurality of links are configured to translate over the biasing mechanism when in the loose configuration.

7. The medical device of claim 1, wherein a distal end of the distalmost link is devoid of any openings through which a tool could pass through, and a circumferential side surface of the distalmost link is devoid of any openings through which a tool could pass through.

8. The medical device of claim 1, wherein, in the compact configuration, a tool lumen extends through each of the plurality of links to permit a tool to extend through the tool lumen.

9. The medical device of claim 1, wherein the plurality of links include a first cross-sectional dimension, and the distalmost link includes a second cross-sectional dimension that is greater than the first cross-sectional dimension, defining an atraumatic distal tip at the distalmost link.

10. The medical device of claim 1, further including an actuation lumen extending at least partially through each of the plurality of links, the actuation member extending through the actuation lumen, and an actuating mechanism configured to apply a proximally directed force to the actuation member to move the plurality of links from the loose configuration to the compact configuration, wherein release of the proximally directed force causes the plurality of links to move from the compact configuration to the loose configuration.

11. The medical device of claim 1, wherein the center lumen and the biasing mechanism extend only partially through the distalmost link of the plurality of links.

12. The medical device of claim 1, further including a light emitting component in the distalmost link of the plurality of links.

13. The medical device of claim 12, wherein the distalmost link includes a transparent material through which the light emitting component emits light.

14. The medical device of claim 1, wherein a proximal end of the distalmost link includes a recess, and a distal end of a proximally adjacent link to the distalmost link includes a tip corresponding in shape to the recess, wherein the recess and the tip prevent radial movement between the distalmost link and the proximally adjacent link in the compact configuration.

15. A medical device, comprising:
an actuation member;
a biasing mechanism;
a plurality of links reciprocally movable between a loose configuration and a compact configuration over the actuation member, the plurality of links being fixed relative to one another when in the compact configuration, and movable relative to one another in the loose configuration; and
a distalmost link positioned distally to the plurality of links, wherein, when in the loose configuration, the distalmost link is configured to remain fixed and the plurality of links are configured to slide relative to one another;
wherein the biasing mechanism is received through a center lumen of each of the plurality of links such that the biasing mechanism is centered in the plurality of links, and the biasing mechanism is offset from an interior surface that defines the center lumen, wherein the biasing mechanism is biased into a longitudinally extended configuration that maintains the plurality of links in the loose configuration.

16. The medical device of claim 15, wherein application of a force to the distalmost link of the plurality of links when the plurality of links are in the loose configuration causes the plurality of links to change orientation relative to one another, and application of the force to the distalmost link when the plurality of links are in the compact configuration does not cause the plurality of links to change orientation relative to one another.

17. The medical device of claim 15, wherein the medical device has a greater length when in the loose configuration than when in the compact configuration.

18. A medical device comprising:
a biasing mechanism;
an actuation member; and
a plurality of links slidably coupled to the actuation member and movable between a loose configuration and a compact configuration;
wherein the biasing mechanism extends through a center lumen extending through each of the plurality of links and is centered relative to the plurality of links, wherein an inner surface of the plurality of links is spaced apart from the biasing mechanism when in the loose and compact configurations and the biasing mechanism is biased into a longitudinally extended configuration that maintains the plurality of links in the loose configuration;
wherein the plurality of links are configured to change orientation relative to one another in response to application of a force to the plurality of links when in the loose configuration, and maintain orientation relative to one another in response to application of the force to the plurality of links when in the compact configuration; and
wherein the plurality of links are configured to translate over the actuation member and the biasing mechanism, and relative to one another when in the loose configuration.

19. The medical device of claim 18, further including a second actuation member coupled to the plurality of links, wherein the actuation member and the second actuation member extend through the plurality of links and are radially offset from the biasing mechanism, such that the biasing mechanism is disposed between the actuation member and the second actuation member.

* * * * *